US011147508B2

(12) United States Patent
Koumpan et al.

(10) Patent No.: US 11,147,508 B2
(45) Date of Patent: Oct. 19, 2021

(54) GENERATING A MATERNAL NUTRITION PLAN FOR PREGNANT WOMEN TO PREVENT FETAL CHRONIC DISEASES

(71) Applicant: INTERNATIONAL BUSINESS MACHINES CORPORATION, Armonk, NY (US)

(72) Inventors: Elezaveta Koumpan, Stoney Creek (CA); Vandana Pandey, Adambakkam (IN); Pamela A. Nesbitt, Ridgefield, CT (US)

(73) Assignee: International Business Machines Corporation, Armonk, NY (US)

( * ) Notice: Subject to any disclaimer, the term of this patent is extended or adjusted under 35 U.S.C. 154(b) by 280 days.

(21) Appl. No.: 16/182,851

(22) Filed: Nov. 7, 2018

(65) Prior Publication Data

US 2020/0138362 A1    May 7, 2020

(51) Int. Cl.
*A61B 5/00* (2006.01)
*G16H 20/60* (2018.01)
*G09B 19/00* (2006.01)

(52) U.S. Cl.
CPC .......... *A61B 5/486* (2013.01); *A61B 5/0011* (2013.01); *A61B 5/4362* (2013.01);
(Continued)

(58) Field of Classification Search
CPC ..... A61B 5/486; A61B 5/0011; A61B 5/4362; A61B 2560/0242; A61B 2503/02; G16H 20/60; G09B 19/0092
See application file for complete search history.

(56) References Cited

U.S. PATENT DOCUMENTS

| 2003/0208113 A1* | 11/2003 | Mault | A61B 5/14532 600/316 |
| 2012/0035958 A1* | 2/2012 | Rhine-Pallas | G06F 19/3456 705/3 |

(Continued)

FOREIGN PATENT DOCUMENTS

| CN | 1745697 A | 3/2006 |
| CN | 104951645 A | 9/2015 |

(Continued)

OTHER PUBLICATIONS

Ip.com, "Algorithm of personalized nutrition prescription for pregnant woman", Disclosure No. IPCOM000249890D, Apr. 25, 2017, pp. 1-2.

(Continued)

*Primary Examiner* — Malina D. Blaise
*Assistant Examiner* — Elizabeth Verniers Johnson
(74) *Attorney, Agent, or Firm* — Caleb D. Wilkes

(57) ABSTRACT

Utilizing a computing device to generate a personalized maternal nutrition plan for a pregnant mother. The computing device receives real-time maternal physiological data, fetal physiological data, and real-time environmental data associated with the pregnant mother. A real-time relationship is established. The real-time relationship is compared with historically established relationships between pregnant mothers and fetuses. The maternal physiological data is compared with pre-pregnancy data of the pregnant mother. The computing device detects one or more abnormalities in the real-time established relationship between the pregnant mother and the fetus based upon the comparison of the real-time established relationship with historically established relationships and the comparison of the maternal physiological data with pre-pregnancy data of the pregnant mother. The computing device generates a maternal nutrition plan. A notification is generated by the computing (Continued)

device and outputted to one or more electronic devices associated with the pregnant mother and/or one or more physicians.

17 Claims, 5 Drawing Sheets

(52) U.S. Cl.
CPC ......... *G09B 19/0092* (2013.01); *G16H 20/60* (2018.01); *A61B 2503/02* (2013.01); *A61B 2560/0242* (2013.01)

(56) References Cited

U.S. PATENT DOCUMENTS

| | | | |
|---|---|---|---|
| 2016/0050962 A1* | 2/2016 | Davies | A23L 33/16 424/646 |
| 2016/0174840 A1* | 6/2016 | Udoh | A61B 5/6804 600/595 |
| 2016/0232326 A1* | 8/2016 | Rydbom | G16H 20/60 |
| 2016/0317341 A1 | 11/2016 | Galvan | |
| 2017/0148348 A1 | 5/2017 | Hardee et al. | |
| 2018/0096739 A1* | 4/2018 | Sano | G16H 40/20 |
| 2019/0119734 A1* | 4/2019 | Harvey | C12Q 1/6834 |

FOREIGN PATENT DOCUMENTS

| | | | | |
|---|---|---|---|---|
| JP | 5850940 B2 | 2/2016 | | |
| WO | WO-2005029242 A2 | * | 3/2005 | ............. G09B 19/00 |
| WO | WO-2013175314 A2 | * | 11/2013 | ........... A61B 5/7275 |
| WO | 2016126645 A2 | | 8/2016 | |
| WO | WO-2018071845 A1 | * | 4/2018 | ............. A61B 5/746 |

OTHER PUBLICATIONS

Google Play, "Ovia Pregnancy Tracker & Baby Countdown Calendar", Apps on Google, https://play.google.com/store/apps/details?id=com.ovuline.pregnancy&h . . . , printed Aug. 17, 2018, pp. 1-3.
Reuters, "Wearable Device Provides Continuous Fetal Monitoring", Science News, Jun. 1, 2015, pp. 1-5.
Zakaria et al., "Fetal Activity Recognition Using 3-Axis Accelerometer Sensor", 2014 IEEE Conference on Biomedical Engineering and Sciences, Dec. 8-10, 2014, Miri, Sarawak, Malaysia, pp. 1-4.
Mell et al., "The NIST Definition of Cloud Computing", National Institute of Standards and Technology, Special Publication 800-145, Sep. 2011, pp. 1-7.
Edawade, "Wearable Pregnancy Monitor Provides Continuous Fetal Monitoring", http://www.iambiomed.com/profile/adityaekawade, printed Nov. 7, 2018, pp. 1-8.

* cited by examiner

GENERATING A MATERNAL NUTRITION PLAN FOR PREGNANT WOMEN TO PREVENT FETAL CHRONIC DISEASES

BACKGROUND

The present invention relates generally to the prevention of fetal chronic diseases, and is more specifically related to generation of a maternal nutrition plan for pregnant woman to prevent the development of chronic diseases in fetuses.

BRIEF SUMMARY

Embodiments of the present invention disclose a method, system, and computer program product for generation of a personalized maternal nutrition plan for a pregnant mother. A computing device receives real-time maternal physiological data associated with a pregnant mother and fetal physiological data. The computing device receives real-time environmental data associated with the pregnant mother. A real-time relationship is established between the maternal physiological data, the fetal physiological data, and the environmental data. The computing device compares the real-time established relationship with historically established relationships between pregnant mothers and fetuses. A comparison is performed of the maternal physiological data with pre-pregnancy data of the pregnant mother. The computing device detects one or more abnormalities in the real-time established relationship between the pregnant mother and the fetus based upon the comparison of the real-time established relationship with historically established relationships and the comparison of the maternal physiological data with pre-pregnancy data of the pregnant mother. The computing device generates a maternal nutrition plan by the computing device based upon the one or more detected abnormalities. A notification is generated by the computing device. The generated notification is outputted to one or more electronic devices associated with the pregnant mother and one or more physicians.

DETAILED DESCRIPTION

Figure 1:
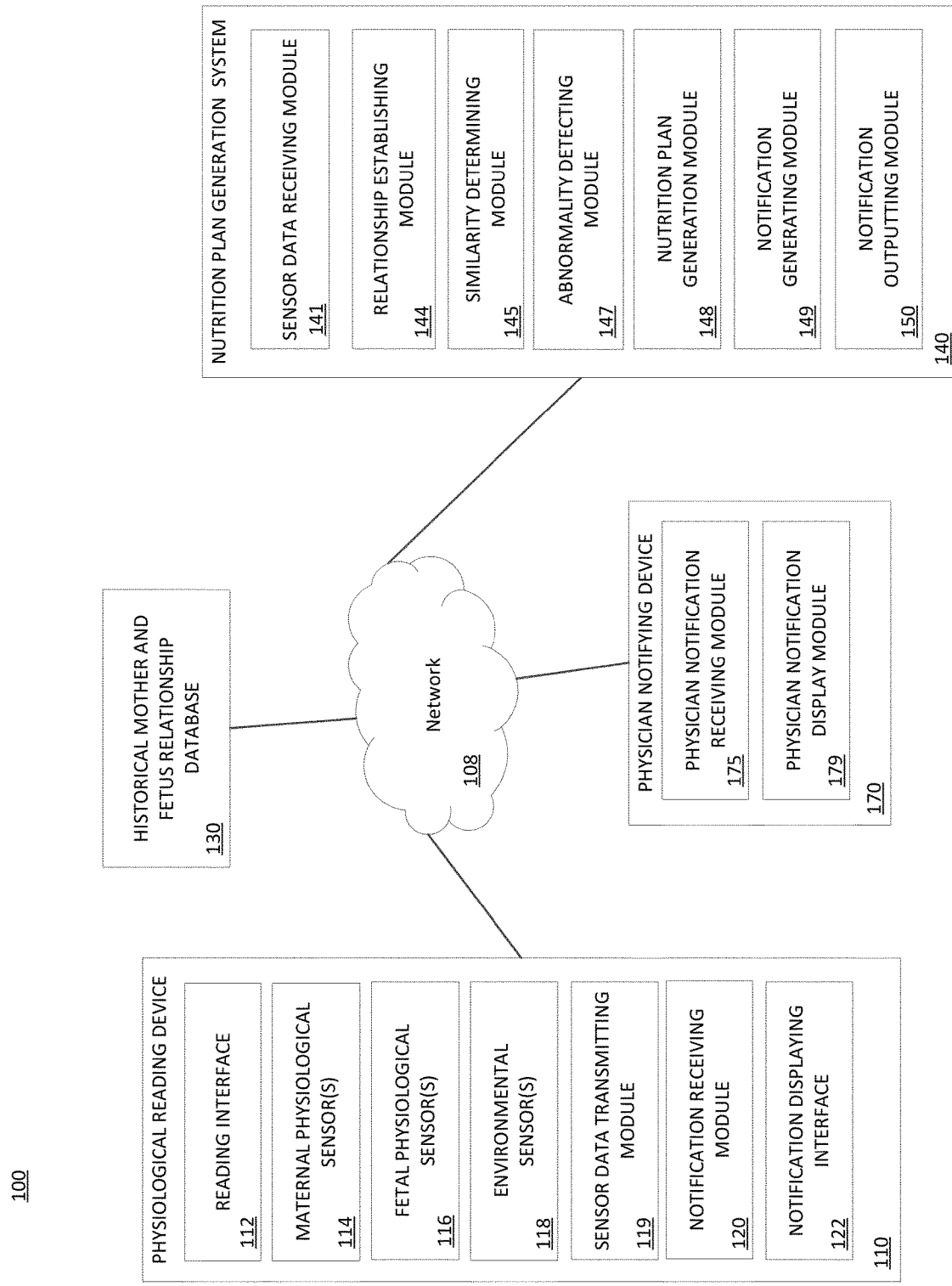
FIG. 1 is a functional block diagram illustrating an environment 100 for generating a maternal nutrition plan, in accordance with an embodiment with the present invention.

Sufficient maternal nutrition is a critical factor in maintaining healthy development of a fetus during a woman's pregnancy. During pregnancy, women require a larger intake of nutrients, including protein, carbohydrates, fats, omega-3 fatty acids, omega-6 fatty acids, iron, iodine, vitamin A, folate, etc. Nutrient deficiencies are associated with complications including, for example, birth defects, and poor post-birth physical and/or mental development. Lifestyle choices of the mother before and during pregnancy such as unhealthy diet and physical inactivity as well as genetic factors such as a predisposition to obesity, metabolic disorders, diabetes of the mother increase the likelihood of these complications. The overconsumption, however, of certain nutrients is also associated with certain developmental or health complications such as an increased likelihood of adulthood diabetes in children whose mothers consumed excessively high amounts of protein and fats during pregnancy. The time of year and environment the mother is in during the time of pregnancy also affects the nutritional needs of the mother and fetus. Mothers, for example, in cold environments or during cold times of the year need to consume more nutrients during cold seasons or in cold weather to maintain her own health and the fetus's development in the womb. Certain tests may be performed on the mother and the growing fetus by a physician to collect data to determine the developmental health of the fetus, the tests including alpha-fetoprotein (AFP) tests, insulin-like growth factor-1 (IGF-1) tests, and ultrasound tests (to indicate the position and movement of the fetus in the womb), but these tests must be performed in person by a physician or other qualified individual, not allowing for real-time information regarding the health and growth of the fetus and/or the health of the mother. Presented are a method, system, and a computer program product for generating by a computing device a personalized maternal nutrition plan in real-time or otherwise.

"Nutrition plan" as discussed herein refers to a computer-provided set or list of nutrients, food, drinks, dietary supplements, vitamins, etc. for a user to intake (or limit intake of) in suggested amounts based on the user's personal needs. The suggested amounts of nutrients, food, drinks, dietary supplements, vitamins, etc. in the set or list may be derived from a user's physiological data including but not limited to heartrate, body temperature, blood pressure, nutrient levels, sugar level, water consumption, body mass index (BMI), diet composition, skin conductance for sweat, body motion, etc. as further discussed herein. For example, the presently disclosed invention may generate a nutrition plan containing nutrients, food, drinks, dietary supplements, vitamins, etc. containing a low amount of sodium to reduce blood pressure because a user's physiological data indicates an "abnormality" of high blood pressure. In the context of the currently disclosed invention, a "maternal nutrition plan" refers to a set of nutrients in suggested amounts for a pregnant woman to consume in order for a fetus in her womb to have healthy development and long-term health.

FIG. 1 is a functional block diagram illustrating an environment 100 for generating a personalized maternal nutrition plan, in accordance with an embodiment with the present invention. In the embodiment displayed in connection with FIG. 1, physiological reading device 110 gathers data from a pregnant mother using various physiological and environmental sensors 114-118 that are present in the embodiment. Physiological reading device 110 may be, in various embodiments, one or more devices such as, for example, a wearable wellness-tracking device, an ultrasound device for capturing sonograms, a heartrate monitor, a genetic information reading device, a blood sugar level monitoring device, a thermometer with electronic functionality, a smart phone, or any computing device possessing sufficient computing power and supporting sufficient functionality to perform the various functions described herein. Physiological reading device 110 outputs the data gathered from sensors 114-118 to nutrition plan generation system 140 for further utilization as described herein. In various embodiments, sensors 114-118, modules 119-120 associated with the sensors 114-118, and interfaces 112, 122 associated with the sensors 114-118 are integrated with the physiological reading device 110 or are separate and connected via a wired or wireless connection with the physiological reading device 110.

Nutrition plan generation system 140 receives, in various embodiments, data from physiological reading device 110, and detects one or more abnormalities in the pregnant mother or the fetus. Nutrition plan generation system 140 generates a maternal nutrition plan for the pregnant mother, as further discussed herein, based upon one or more abnormalities detected by the nutrition plan generation system 140. As displayed in FIG. 1, in addition to receiving physiological data and environmental data from the physiological reading device 110 to generate the maternal nutrition plan, nutrition plan generation system 140, in various embodiments of the invention, also accesses historical mother and fetus relationship database 130 to obtain historically established relationships between pregnant mothers and fetuses, which are further utilized as discussed herein. In various embodiments, after generation of the personalized maternal nutrition plan by nutrition plan generation system 140, nutrition plan generation system 140 generates and transmits to physiological reading device 110 a notification to notify one or more individuals of the generation of the nutrition plan. In various embodiments, nutrition plan generation system 140 also detects and notifies various individuals of one or more abnormalities in the physiology of the pregnant mother or the unborn child (as further discussed herein), including a physician, dietitian, or other medical professional associated with physician notifying device 170.

All of physiological reading device 110, historical mother and fetus relationship database 130, nutrition plan generation system 140, and physician notifying device 170 are connected via a network 108. In various embodiments, network 108 represents, for example, an Internet, a local area network (LAN), a wide area network (WAN) such as the Internet, and includes wired, wireless, or fiber optic connections. In general, network 108 may be any combination of connections and protocols that will support communications between physiological reading device 110, historical mother and fetus relationship database 130, nutrition plan generation system 140, and physician notifying device 170, in accordance with an embodiment of the invention.

Physiological reading device 110, historical mother and fetus relationship database 130, nutrition plan generation system 140, and physician notifying device 170 may perform various steps as discussed in connection with FIG. 2, and include internal and external hardware components as depicted and described further in detail with reference to FIG. 3, below (and as otherwise discussed herein). Physiological reading device 110, historical mother and fetus relationship database 130, nutrition plan generation system 140, and physician notifying device 170 may be, for example, a mainframe or a mini computer, a terminal, or any other sort of computing device (or as otherwise described herein). In other embodiments, each of physiological reading device 110, historical mother and fetus relationship database 130, nutrition plan generation system 140, and physician notifying device 170 may be implemented in a cloud computing environment, as described in relation to FIGS. 4 and 5, below (or, again, as otherwise described herein). In a still further embodiment, some or all of physiological reading device 110, historical mother and fetus relationship database 130, nutrition plan generation system 140, and physician notifying device 170 are embodied in physically the same computing device, with all communications between various components made internally.

In an embodiment of the invention, physiological reading device 110 comprises a reading interface 112, maternal physiological sensor(s) 114, fetal physiological sensor(s) 116, environmental sensor(s) 118, sensor data transmitting module 119, a notification receiving module 120, and a notification displaying module 122. As discussed previously, physiological reading device 110 may be, in various embodiments, one or more devices such as, for example, a wearable wellness-tracking device, an ultrasound device for capturing sonograms, a heartrate monitor, a genetic information reading device, a blood sugar level monitoring device, a thermometer with electronic functionality, a smart phone, or any computing device possessing sufficient computing power and supporting sufficient functionality to perform the various functions described herein. Sensor(s) 114, 116, 118 may be integrated with physiological reading device 110 or separate and connected via a wired or wireless connection.

Reading interface 112 represents a software and/or hardware interface, such as a graphical user interface (GUI) displayed such as with display screen 920 to allow a user to review information presented to an individual and make selections. In an embodiment of the invention, one or more abnormalities and/or the personalized maternal nutrition plan are presented from the nutrition plan generation system 140 to a user via the reading interface 112. Reading interface 112 may also present further information to the user, including foods, drinks, vitamins, and/or other dietary supplements to consume to address one or more abnormalities, as well as a schedule of when to consume them in order for the user to comply with the personalized maternal nutrition plan presented to the individual. The reading interface 112 may also be used to allow the user to make selections regarding the maternal nutrition plan, such as a choice of several foods, drinks, vitamins or other dietary supplements to consume to comply with the personalized maternal nutrition plan. In various embodiments of the invention, reading interface 112 may also present to the user real-time collected maternal physiological data, fetal physiological data, and environmental data after collection in real-time, as further discussed herein.

Maternal physiological sensor(s) 114 represents a hardware and/or software component integrated with physiological reading device 110, or separate from physiological reading device 110 and connected to physiological reading device 110 via a wired or wireless connection that detects and measures maternal physiological data. In various embodiments of the invention, one or more maternal physiological sensor(s) 114 may measure in real-time one or more of a mother's heartrate, body temperature, blood pressure, various nutrient levels, blood sugar level, water consumption, body mass index (BMI), diet composition, skin conductance for sweat, frequency of motion, various biochemical data, and/or other data. Physiological reading device 110 may display the maternal physiological data taken by the maternal physiological sensor(s) 114 to a user via reading interface 112. In an embodiment of the invention, maternal physiological sensor(s) 114 outputs the maternal physiological data to the nutrition plan generation system 140 via network 108 for further utilization as described herein. In the various embodiments of the invention, maternal physiological sensor(s) 114 may be sensors for measuring any of the maternal physiological data provided above.

Fetal physiological sensor(s) 116 represents a hardware and/or software component integrated with physiological reading device 110, or separate from physiological reading device 110 and connected to physiological reading device 110 via a wired or wireless connection that detects and measures fetal physiological data. In various embodiments of the invention, one or more fetal physiological sensor(s) 116 may measure in real-time one or more of fetal heartrate, fetal movement in the womb, fetal position in the womb, size of fetus, genetic data, possible infections, various biochemical data, etc. Physiological reading device 110 may display the fetal physiological data taken from fetal physiological sensor 116 to a user via reading interface 112. In various embodiments of the invention, fetal physiological sensor 116 outputs the fetal physiological data to the nutrition plan generation system 140 via network 108 for further utilization as described herein. In various embodiments of the invention, fetal physiological sensor(s) 116 may be one or more of an electronic heartrate sensor or an ultrasound device to take sonograms of the fetus's position and movement in the womb, a DNA sequence reading device, a chromosomal reading device, an alpha-fetoprotein (AFP) detecting device, or an insulin-like growth factor-1 (IGF-1) reading device. Fetal physiological sensor 116 may receive fetal physiological data on a scheduled basis, in real-time, or otherwise.

Environmental sensor(s) 118 represents a hardware component and/or a software component integrated with physiological reading device 110, or separate from physiological reading device 110 and connected to physiological reading device 110 via a wired or wireless connection that detects and measures environmental data associated with the pregnant mother in real-time including but not limited to ambient temperature, humidity, wind speed, pollution levels, and light intensity. The environmental sensor(s) 118 may be one or more of thermometer(s), humidity sensor(s), anemometer(s), pollution sensor(s), and/or light sensor(s). Physiological reading device 110 may display the environmental data taken from environmental sensor 118 to a user via reading interface 112. In various embodiments of the invention, environmental sensor(s) 118 outputs the environmental data to the nutrition plan generation system 140 via network 108, for further utilization as discussed herein.

Sensor data transmitting module 119 represents a hardware and/or software component associated with physiological reading device 110 for transmitting maternal physiological data, fetal physiological data, and/or environmental data (whichever are available and utilized in the embodiment of the invention under consideration) to nutrition plan generating system 140 for further utilization. Maternal physiological data, fetal physiological data, and/or environmental data is collected by maternal physiological sensor(s) 114, fetal physiological sensor(s) 116, and environmental sensor(s) 118 as further discussed herein.

Notification receiving module 120 represents a hardware and/or software component associated with physiological reading device 110 that receives a notification from nutrition plan generation system 140, such as via a push notification generated by nutrition plan generation system 140, as discussed further herein. The push notification is further discussed herein. Alternatively, notification receiving module 120 may receive notification from nutrition plan generation system 140 via an e-mail, via a text message, within an application program designed for such purposes (and executing on physiological reading device 110), via a web page, via a plug-in or add on to web browser, or in another equivalent manner as further discussed herein.

Notification displaying interface 122 represents an interface such as a display screen 920 displaying a graphical user interface (GUI) for a user at physiological reading device 110 to view data presented to him or her, and make selections via the GUI. After receipt of notification, notification displaying interface 122 may display the notification in the form of a text message, an image-based message, an audio playback, a video playback, etc. for viewing by the user. In alternative embodiments of the invention, notification displaying interface 122 may simply display the notification to the user without offering selections to the user via a GUI.

In an embodiment of the invention, nutrition plan generation system 140 serves to generate a personalized maternal nutrition plan as further discussed herein. In an embodiment of the invention, nutrition plan generation system 140, comprises a sensor data receiving module 141, a relationship establishing module 144, a similarity determining module 145, an abnormality detecting module 147, a nutrition plan generation module 148, a notification generating module 149, and a notification outputting module 150.

Sensor data receiving module 141 represents hardware and/or software for receiving from the sensor data transmitting module 119 of physiological reading device 110 maternal physiological data, fetal physiological data, and/or environmental data collected by maternal physiological sensor(s) 114, fetal physiological sensor(s) 116, and environmental sensor(s) 118 (whichever are present in the embodiment of the invention). Maternal physiological data, fetal physiological data, and environmental data are processed by the computing device associated with the nutrition plan generation system 140, as further discussed herein.

Relationship establishing module 144 represents hardware and/or software for establishing a real-time relationship between the maternal physiological data, the fetal physiological data, and the environmental data (whichever are present in the embodiment of the invention). Relationship establishing module 144 may utilize a matching algorithm, artificial intelligence, cognitive computing, a ranking algorithm, a best-fit analysis performed by nutrition plan generating system 140, or any other computer-implemented means to establish a correlation between available maternal physiological data, fetal physiological data, and/or environmental data in real-time (i.e., as the data is received from the sensor data transmitting module 119). Relationship establishing module 144 may also utilize maternal physiological data, fetal physiological data, and/or environmental data which has been previously collected from maternal physiological sensor(s) 114, fetal physiological sensor(s) 116, and environmental sensor(s) 118 in making determinations regarding the real-time relationship for the generation of a nutrition plan, as further discussed herein. The real-time relationship established may indicate "trends" in data, which are utilized as further discussed herein. The real-time relationship established may, for example, indicate a high level of triglycerides in the blood chemistry of the pregnant mother (as displayed by the maternal physiological data) and a corresponding high level of triglycerides displayed by the fetus (as displayed by the fetal physiological data). The real-time relationship established by relationship establishing module 144 may be further utilized as discussed herein.

Similarity determining module 145 represents hardware and/or software for nutrition plan generation system 140 to compare the real-time established relationship (established by the relationship establishing module 144, as discussed above), with historically established relationships between pregnant mothers and fetuses obtained from the historical mother and fetus relationship database 130, for further utilization as described herein. Similarity determining module 145 may rely on any of a matching algorithm, artificial intelligence, cognitive computing, a ranking algorithm, a best-fit analysis performed by nutrition plan generating system 140, or any other computer-implemented means to compare the real-time established relationship with one or more historically established relationships between pregnant mothers and fetuses. In comparing the real-time established relationship with historically established relationships, similarity determining module 145, in effect, seeks similar data points available to "match" the real-time established relationships with the one or more established relationships which are most similar for further utilization as discussed herein. In an embodiment of the invention, similarity determining module 145 may, after accessing a plurality of historically established relationships between pregnant mothers and fetuses from the historical mother and fetus relationship database 130, determine degrees of similarity of the historically established relationships to the real-time established relationship via utilization of a ranking algorithm, and select one or more historically established relationships with the highest degree of similarity to the established real-time relationship, for further utilization by the abnormality detecting module 147 in detecting abnormalities.

Similarity determining module 145 of nutrition plan generation system 140, in an embodiment of the invention, also compares maternal physiological data obtained from the sensor data transmitting module 119 to pre-pregnancy data obtained from the historical mother and fetus relationship database 130 to locate similarities in data available, for further utilization as described herein in detecting abnormalities. In effect, when similarity determining module 145 compares maternal physiological data to pre-pregnancy data, the presently disclosed invention takes account of unique data available for the pregnant mother, including unique medical conditions and other medical data available for the individual. As previously, the similarity determining module 145 may rely on any of a matching algorithm, artificial intelligence, cognitive computing, a ranking algorithm, a best-fit analysis performed by nutrition plan generating system 140, or any other computer-implemented means to locate similarities in pre-pregnancy data available and the maternal physiological data.

Abnormality detecting module 147 represents software and/or hardware for nutrition plan generation system 140 to detect one or more abnormalities utilizing the data obtained from the relationship establishing module 144 and as otherwise described herein. An "abnormality," as discussed herein is a deviation from a regular, recommended, or ideal health state for a similar individual with regard to a nutrient, blood physiology, health conditional state, etc. for a healthy person without preexisting genetic, developmental, or other health disorders. Abnormalities as discussed herein may affect the mother or fetus. In various embodiments of the invention, an abnormality may be a quantitative or qualitative deviation from a preconfigured physiological metric for a healthy person, indicated as further discussed herein. Types of abnormalities determined by the abnormality detecting module 147 may include, but are not limited to, fast or slow maternal or fetal heartrate, under or over consumption of water or a particular nutrient, high or low blood pressure, a DNA sequence indicating a genetic defect, a chromosomal defect, a high AFP level, exposure to high levels of pollutants, high or low body temperature, high skin conductance from large amounts of sweat, etc. In one example, abnormality detecting module 147 may detect an abnormality for high blood pressure in the mother in the real-time relationship between mother and fetus because a historical mother and fetus relationship 310 with a high degree of similarity is comprised of an abnormality for high blood pressure. In this example, an abnormality for high blood pressure is flagged, recorded by the abnormality detecting module 147, and utilized as further discussed herein.

Abnormalities detected by the abnormality detecting module 147, in an embodiment of the invention, may be based upon the comparison of the real-time established relationship with historically established relationships performed by the similarity determining module 145, as well as (if present) the comparison of the maternal physiological data with pre-pregnancy data of the pregnant mother also performed by the similarity determining module 145. Abnormality detecting module 147 utilizes correlations established by the abnormality detecting module 147 in data (and other comparisons as discussed herein) to pinpoint abnormalities which have developed, or are likely to develop, in the pregnant mother and/or unborn child. Abnormality detecting module 147 may, for example, detect abnormalities such as too high a level of a bionutrient, or too low a level of a bionutrient based upon whether the real-time established relationship displays bionutrient data which differs from an accepted range of bionutrient data established by the historically established relationships. Similarly, abnormality detecting module 147 may notice a notice a heartbeat which is too fast on average based upon comparisons between the real-time established relationship and the historically established relationships. Since, in various embodiments, abnormalities previously experienced by individuals are displayed by the historically established relationships, abnormality detecting module 147 may be able to directly predict which abnormalities have already resulted or likely will result, depending upon the levels bionutrients or other data. Abnormalities detected may be a qualitative or quantitative deviation from a preconfigured metric for a healthy person (the preconfigured metrics may be indicated in the historically established relationships, or otherwise). In various embodiments of the invention, abnormalities detected by the abnormality detecting module 147 are stored for later use, as further discussed herein, and transmitted to the user or a medical professional. Abnormality detection module 147 may additionally utilize pre-pregnancy data of the pregnant mother to indicate whether the pre-pregnancy data implies one or more abnormalities existed prior to pregnancy, which may be considered by the abnormality detection module 147 in determining whether a current abnormality exists in the individual. If, for example, pre-pregnancy data indicates an individual has a blood sugar abnormality, current data indicated by the real-time established relationships may imply a current abnormality does not actually exist, at least for the individual in question.

Nutrition plan generation module 148 represents hardware and/or software for nutrition plan generation system 140 to generate a maternal nutrition plan based upon one or more abnormalities detected by the abnormality detecting module 147. After detection of abnormalities in the mother or fetus, in a manner as discussed herein, nutrition plan generation module 148 accesses a local database, remote database, or other store of data where nutritional information regarding foods, drinks, nutritional supplements, vitamins, etc. is stored. Nutrition plan generation module 148 utilizes the nutritional information regarding foods, drinks, nutrition supplements, vitamins, etc. to automatically generate a nutrition plan to counter and/or prevent the one or more abnormalities previously detected by the abnormality detecting module 147. If, for example, abnormality detecting module 147 detects a low value of vitamin c, nutrition plan generation module 148 generates a nutrition plan high in vitamin c rich foods such as oranges, lemons, or recommends a vitamin c supplement. If abnormality detecting module 147 detects an abnormally high heart beat, on average, nutrition plan generation module 148 may generate a nutrition plan low in caffeine for the pregnant mother. In various embodiments of the invention, the nutrition plan generated by nutrition plan generation module 148 may contain a set or list of nutrients in suggested amounts for the pregnant mother to intake for healthy development and long-term health of the fetus based on the one or more detected abnormalities (or, nutrients to limit). In the example provided previously, where an abnormality for high blood pressure is detected, the maternal nutrition plan generated by the nutrition plan generation module 148 may contain a set or list of nutrients in suggested amounts for the mother to lower her blood pressure, including lower amounts of sodium and higher amounts of potassium, as well as higher amounts of water. In the various embodiments, the maternal nutrition plan generated by the nutrition plan generation module 148 is further utilized by the presently disclosed invention as discussed herein, and may be generated on an hourly basis, daily basis, a weekly basis, or a monthly based upon the needs of the pregnant mother (such as an irregular blood sugar level, which would require frequent monitoring, by means of non-limiting example).

Notification generation module 149 represents hardware and/or software for nutrition plan generation system 140 to generate a notification for utilization as discussed herein. The notification includes the personalized maternal nutrition plan generated by the nutrition plan generation module 148 and/or the one or more detected abnormalities detected by the abnormality detecting module 147. The notification generated by notification generation module 149, in various embodiments of the invention, takes any computerized form capable of being transmitted across network 108 or made available in any manner to physiological reading device 110 and/or physician notifying device 170, as further discussed herein.

Notification outputting module 150 represents software and/or hardware for nutrition plan generation system 140 to transmit and/or make available in another way the notification generated by notification generation module 149 containing the personalized maternal nutrition plan and/or the one or more detected abnormalities to the physiological reading device 110 and/or the physician notifying device 170. The notification generated by notification generation module 149 is transmitted, in various embodiments, to the notification receiving module 120 of physiological reading device 110 and/or the physician notification receiving module 175 of physician notifying device 170. The notification transmitted by the notification outputting module 150 may be embodied in the form of a push notification, an e-mail, a text message, an electronic message within an application executing entirely or partially on nutrition plan generation system 140, physiological reading device 110, or physician notifying device 17, via a web page, via a plug-in to a web browser, or in another equivalent manner. A push notification generated by notification generation module 149 presents the advantage of appearing on the physiological reading device 110 and/or the physician notifying device 170 for display on these devices without having to wait for the physiological reading device 110 and/or the physician notifying device 170 to poll the nutrition plan generation system 140 (or another computer system acting as a server) to obtain the personalized maternal nutrition plan, which may not occur very rapidly.

As also displayed in the environment 100, in an embodiment of the invention as displayed in FIG. 1, a historical mother and fetus relationship database 130 is also present. The historical mother and fetus relationship database 130 is an electronic archive (such as available from a computerized database or similar computerized means of storing electronic data) containing one or more historically established relationships between pregnant mothers and fetuses, including associated data. In an embodiment of the invention, historical mother and fetus relationship database 130 may contain a large number of historically established relationships between pregnant mothers and fetuses, for further utilization as discussed herein. The historically established relationships between pregnant mothers and fetuses may contain abnormalities displayed by the pregnant mother and/or fetus (and when they were experienced), as well as contain, for example, various maternal physiological data recorded at different times during pregnancy such as, for example, weight, body-fat percentage, blood sugar levels, glyceride levels, heartrate, body temperature, skin conductivity, blood pressure, various biochemical tested for, infection data, conditions, diseases, etc.), as well as fetal physiological data recorded at different times during pregnancy including, for example, fetal heartrate, sonogram data, amniotic biochemical data, fetal movement in the womb, fetal position in the womb, size of fetus, genetic data, infection data, other biochemical data, etc. The historically established relationships may include environmental data associated with the pregnant mother at different times during pregnancy such as, for example, ambient temperature, humidity, wind speed, pollution levels, light intensity, etc. Historically established relationships stored by the historical mother and fetus relationship database 130 are maintained according to times when the maternal physiological data, fetal physiological data, and/or environmental data is available, to indicate possible causation allowing the historically established relationships to be further utilized for comparison with established real-time relationships established by the nutrition plan generation system 140, as further discussed herein.

In an embodiment of the invention, historical mother and fetus relationship database 130 may also contain (or have access to) maternal pre-pregnancy data regarding one or more individuals (including the individual utilizing the presently disclosed invention and/or other individuals). The pre-pregnancy data may contain, by means of non-limiting example, abnormalities experienced (and when they were experienced), as well as age, genetic data, personal medical history, physical activity, use of nutritional supplements, lifestyle, physical examination data, pre-pregnancy weight, pre-pregnancy body-fat percentage, blood sugar levels, glyceride levels, heartrate, body temperature, blood pressure, various biochemical tested for in the blood, infection data, conditions, diseases, etc. The pre-pregnancy data stored by the historical mother and fetus relationship database 130 is further utilized as discussed herein.

In an embodiment of the invention, also displayed in environment 100 is physician notification device 170. A physician, dietitian, or other medical professional may utilize the physician notifying device 170 to receive notifications as further discussed herein, to aid in providing medical care for the pregnant mother. In an embodiment of the invention, physician notifying device 170 comprises a physician notification receiving module 175 and a physician notification display module 179. As discussed elsewhere herein, the notification may contain the personalized maternal nutrition plan generated by the nutrition plan generation module 148 and/or the one or more detected abnormalities detected by the abnormality detecting module 147, allowing the physician, dietitian, or other medical professional to review the personalized maternal nutrition plan and provide further medical advice and/or treatment, as required. Physician notifying device 170 may be any sort of computing device capable of receiving notifications such as described herein, such as by means of a non-limiting example, a smartphone, a personal computer, a tablet computer, etc., or even an internet browser executing on one of these devices, etc.

Physician notification receiving module 175 represents software and/or hardware for receipt of a notification generated by the nutrition plan generation system 140. The notification is generated by the notification generating module 149 and transmitted to the physician notifying device 170 via the notification outputting module 150 (as further discussed herein). As discussed elsewhere herein, the notification generated by the nutrition plan generation system 140 takes different forms in various embodiments of the invention, such as a push notification, etc.

Physician notification display module 179 represents software and/or hardware for display of the notification to the physician, dietitian, other medical professional, etc., allowing for the providing of further medical care, treatment, etc. Physician notification display module 179 may take different forms in different embodiments of the invention, such as an application executing at least in part on the physician notifying device 170, an e-mail program, a text message receiving program, a web browser, etc. with the form of physician notification display module 179 dependent upon the form of the notification, as discussed further herein.

Figure 2:
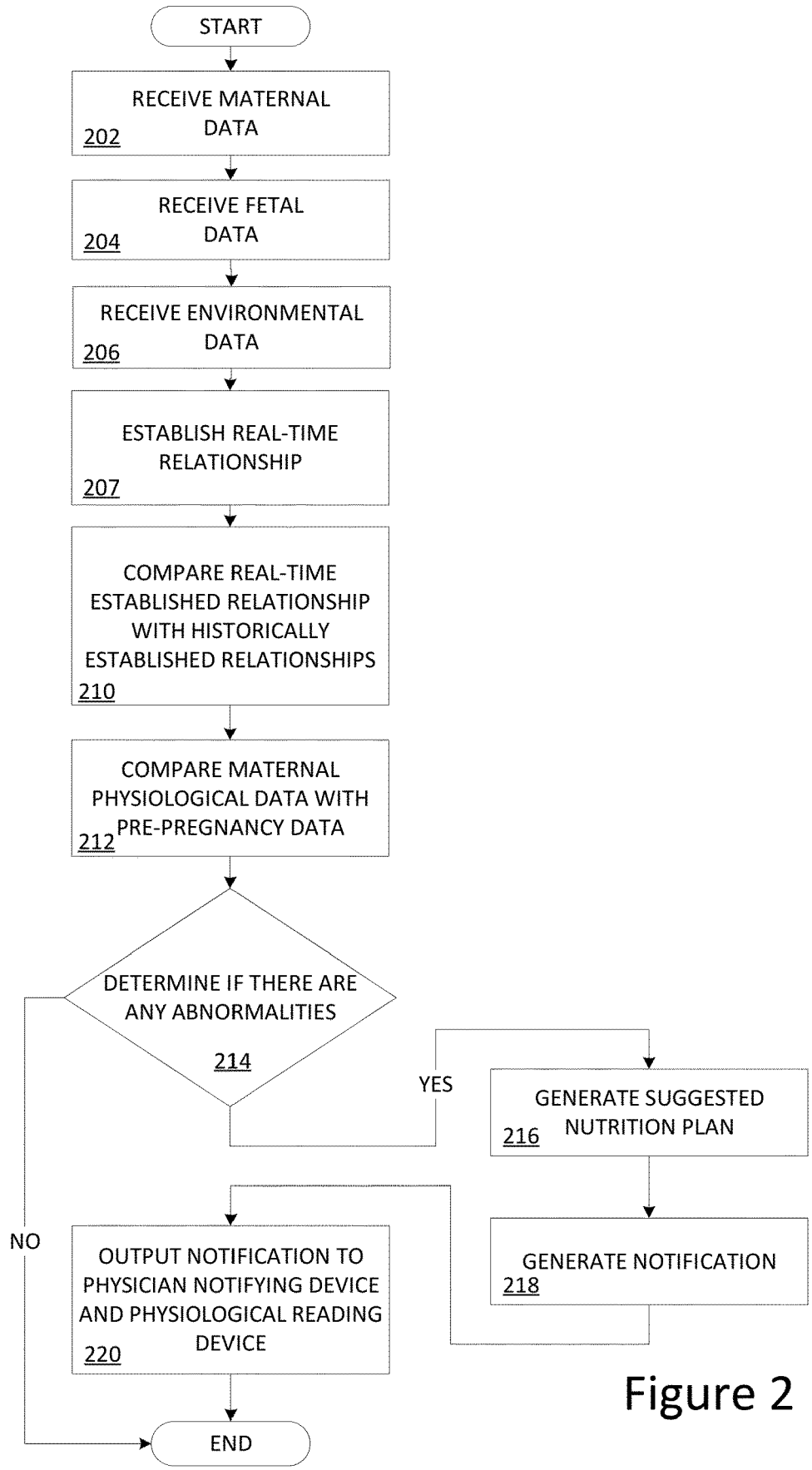
FIG. 2 is a flowchart depicting operational steps of a nutrition plan generation system 140, in accordance with an embodiment with the present invention.

FIG. 2 is a flowchart depicting operational steps performed by nutrition plan generation system 140, in accordance with an embodiment of the present invention. At step 202 sensor data receiving module 141 of nutrition plan generation system 140 receives maternal physiological data associated with a pregnant mother from sensor data transmitting module 119 of physiological reading device 110. At step 204, sensor data receiving module 141 of nutrition plan generation system 140 receives fetal physiological data from sensor data transmitting module 119. At step 206, sensor data receiving module 141 of nutrition plan generation system 140 receives environmental data associated with the pregnant mother from sensor data transmitting module 119 of physiological reading device 110. At step 207, a real-time relationship is established by the relationship establishing module 144 between the maternal data, fetal data, and environmental data. At step 210, the similarity determining module 145 compares the real-time established relationship with historically established relationships between pregnant mother and fetuses, the historically established relationships obtained from the historical mother and fetus relationship database 130. At step 212, similarity determining module 145 compares maternal physiological data with pre-pregnancy data of the pregnant mothers. At step 214, abnormality detecting module 147 of nutrition plan generation system 140 detects any abnormalities in the real-time established relationship between the pregnant mother and the fetus based upon the comparison of the real-time established relationship with historically established relationships (from step 210) and the comparison between the maternal physiological data with pre-pregnancy data of the pregnant mother (from step 212). If there are not abnormalities detected, execution may proceed to end. If there are one or more abnormalities detected, execution proceeds to step 216 where nutrition plan generation module 148 generates a suggested maternal nutrition plan based upon the one or more abnormalities. At step 218, notification generating module 149 generates a notification containing information about the one or more abnormalities and/or the maternal nutrition plan. At step 220, the notification is transmitted to the notification receiving module 120 of the physiological reading device 110 and/or the physician notification receiving module 175 of the physician notification device 170. Execution proceeds to end, as is displayed in FIG. 2.

Figure 3:
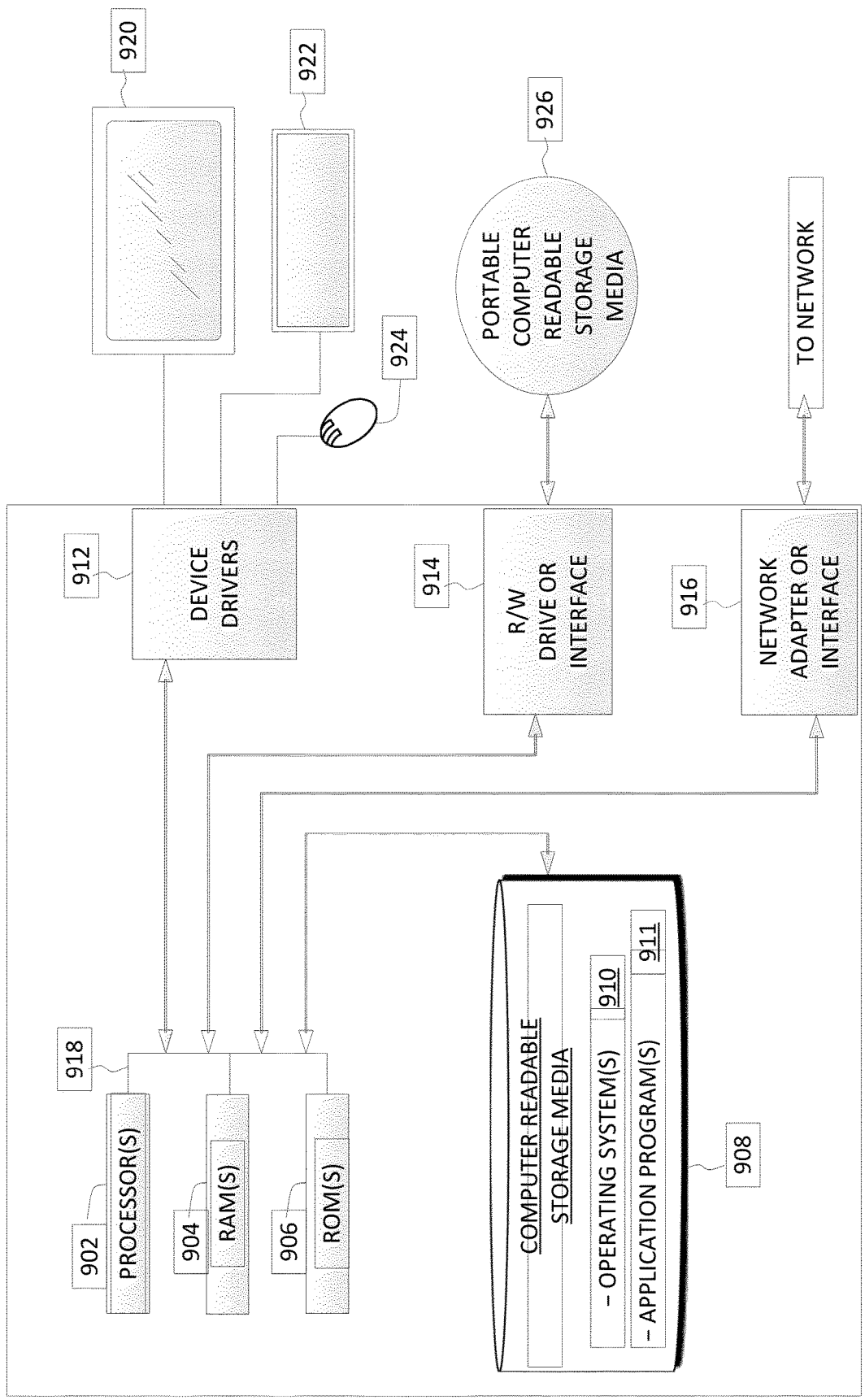
FIG. 3 depicts a block diagram of components of a physiological reading device 110, historical mother and fetus relationship database 130, nutrition plan generation system 140, and physician notifying device 170, in accordance with an embodiment of the present invention.

FIG. 3 depicts a block diagram of components of physiological reading device 110, historical mother and fetus relationship database 130, nutrition plan generation system 140, and physician notifying device 170 in the environment 100 for generating a personalized maternal nutrition plan in accordance with an embodiment of the present invention. It should be appreciated that FIG. 3 provides only an illustration of one implementation and does not imply any limitations with regard to the environments in which different embodiments may be implemented. Many modifications to the depicted environment may be made.

Physiological reading device 110, physician notifying device 170, historical mother and fetus relationship database 130, and nutrition plan generation system 140 may include one or more processors 902, one or more computer-readable RAMs 904, one or more computer-readable ROMs 906, one or more computer readable storage media 908, device drivers 912, read/write drive or interface 914, network adapter or interface 916, all interconnected over a communications fabric 918. Communications fabric 918 may be implemented with any architecture designed for passing data and/or control information between processors (such as microprocessors, communications and network processors, etc.), system memory, peripheral devices, and any other hardware components within a system.

One or more operating systems 910, and one or more application programs 911, for example, the environment for generating a maternal nutrition plan, are stored on one or more of the computer readable storage media 908 for execution by one or more of the processors 902 via one or more of the respective RAMs 904 (which typically include cache memory). In the illustrated embodiment, each of the computer readable storage media 908 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Physiological reading device 110, historical mother and fetus relationship database 130, nutrition plan generation system 140, and physician notifying device 170 may also include a R/W drive or interface 914 to read from and write to one or more portable computer readable storage media 926. Application programs 911 on media playing device 110, reading device 120, media network 130, and nutrition plan generation system 140 may be stored on one or more of the portable computer readable storage media 926, read via the respective R/W drive or interface 914 and loaded into the respective computer readable storage media 908.

Physiological reading device 110, historical mother and fetus relationship database 130, nutrition plan generation system 140, and physician notifying device 170 may also include a network adapter or interface 916, such as a TCP/IP adapter card or wireless communication adapter (such as a 4G wireless communication adapter using OFDMA technology). Application programs 911 on physiological reading device 110, historical mother and fetus relationship database 130, nutrition plan generation system 140, and physician notifying device 170 may be downloaded to the computing device from an external computer or external storage device via a network 108 (for example, the Internet, a local area network or other wide area network or wireless network) and network adapter or interface 916. From the network adapter or interface 916, the programs may be loaded onto computer readable storage media 908. The network may comprise copper wires, optical fibers, wireless transmission, routers, firewalls, switches, gateway computers and/or edge servers.

Physiological reading device 110, historical mother and fetus relationship database 130, nutrition plan generation system 140, and physician notifying device 170 may also include a display screen 920, a keyboard or keypad 922, and a computer mouse or touchpad 924. Device drivers 912 interface to display screen 920 for imaging, to keyboard or keypad 922, to computer mouse or touchpad 924, and/or to display screen 920 for pressure sensing of alphanumeric character entry and user selections. The device drivers 912, R/W drive or interface 914 and network adapter or interface 916 may comprise hardware and software (stored on computer readable storage media 908 and/or ROM 906).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a method, computer program product, and/or computer system at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, computer program products, and apparatus (systems) according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of method, system, and computer program product according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
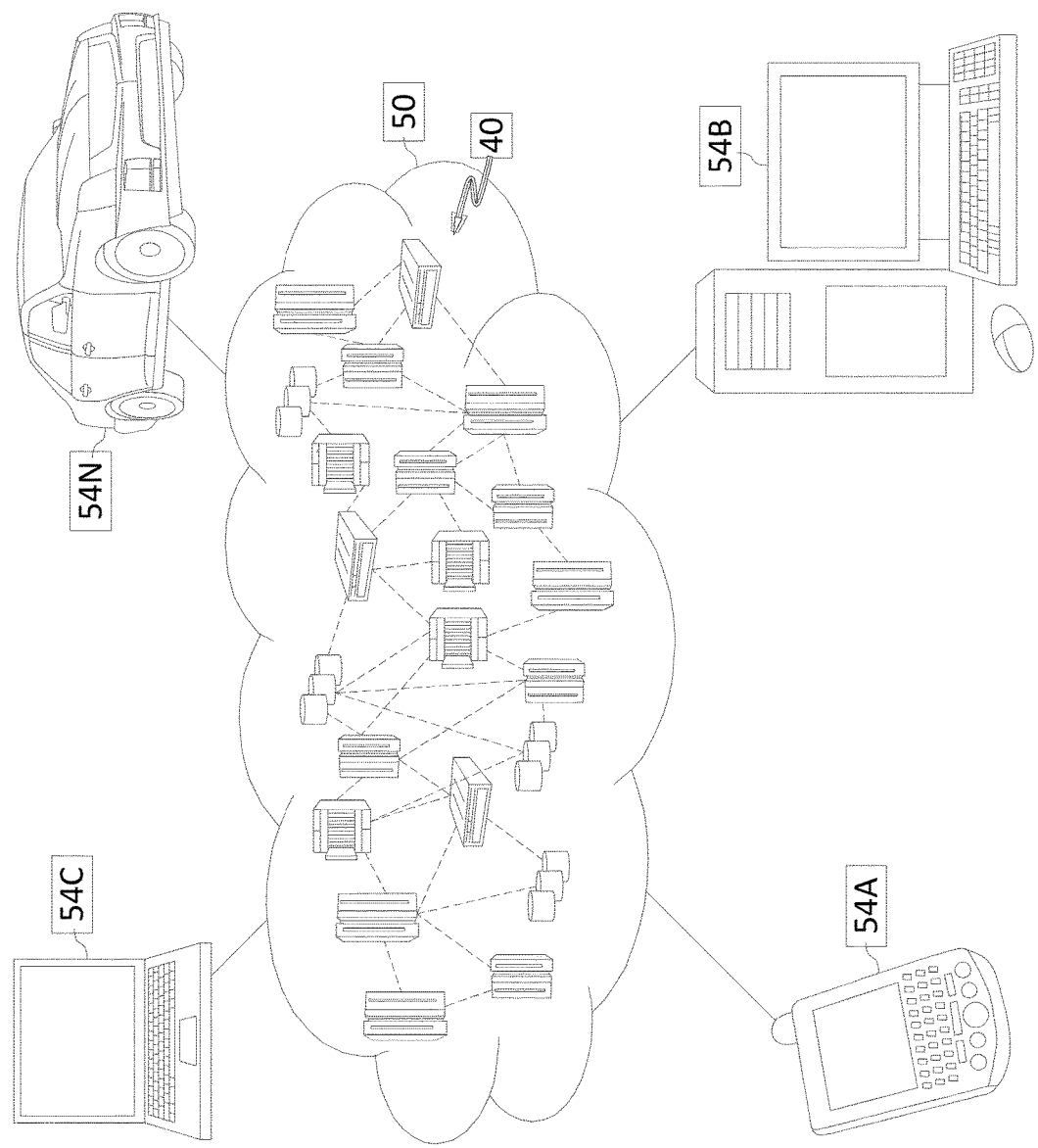
FIG. 4 depicts a cloud computing environment, in accordance with an embodiment of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 5:
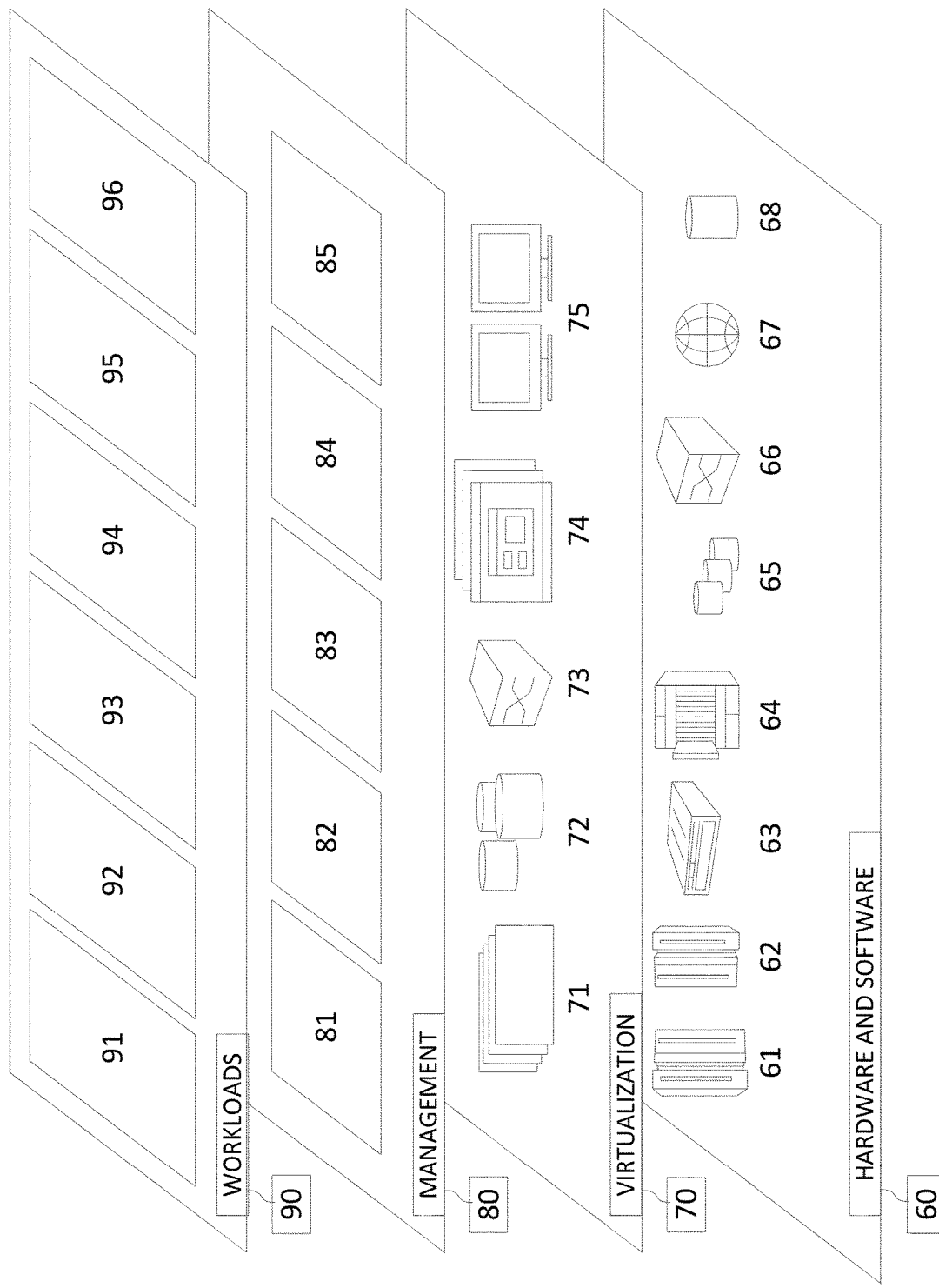
FIG. 5 depicts abstraction model layers, in accordance with an embodiment of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA. Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and the environment 100 for generating a maternal nutrition plan.

Based on the foregoing, a method, system, and computer program product have been disclosed. However, numerous modifications and substitutions can be made without deviating from the scope of the present invention. Therefore, the present invention has been disclosed by way of example and not limitation.

What is claimed is:

1. A method for utilizing a computing device to generate a personalized maternal nutrition plan for a pregnant mother, the method comprising:
   receiving by a computing device real-time maternal physiological data associated with a pregnant mother and real-time fetal physiological data from a fetus within the pregnant mother, wherein the real-time maternal physiological data is detected via a first sensor and comprises a maternal triglyceride level, and wherein the real-time fetal physiological data is detected via a second sensor and comprises a fetal triglyceride level;
   receiving, by the computing device, real-time environmental data associated with the pregnant mother, wherein the real-time environmental data is detected via a third sensor and is selected from the group consisting of humidity and wind speed;
   establishing by the computing device a real-time relationship between the maternal physiological data, the fetal physiological data, and the environmental data, wherein the real-time relationship comprises a triglyceride relationship of the maternal triglyceride level with respect to the fetal triglyceride level;
   comparing the real-time established relationship with historically established relationships between pregnant mothers and fetuses;
   comparing the maternal physiological data with pre-pregnancy data of the pregnant mother;
   detecting by the computing device of one or more abnormalities in the real-time established relationship between the pregnant mother and the fetus based upon the comparison of the real-time established relationship with historically established relationships and the comparison of the maternal physiological data with pre-pregnancy data of the pregnant mother;
   generating a maternal nutrition plan by the computing device based upon the one or more detected abnormalities, wherein the maternal nutrition plan comprises a list of nutrients in suggested amounts for the pregnant mother to intake and a schedule of when to consume the nutrients;
   outputting the generated maternal nutrition plan and the detected one or more abnormalities to a first electronic device associated with the pregnant mother and to a second electronic device associated with a physician; and
   presenting the maternal nutrition plan and the one or more abnormalities via the first electronic device and via the second electronic device.

2. The method of claim 1, wherein the comparing the real-time established relationship with historically established relationships comprises:
   accessing, by the computing device, a plurality of historically established relationships between pregnant mothers and fetuses; and
   selecting, by the computing device, one or more historically established relationships with a highest degree of similarity to the established real-time relationship.

3. The method of claim 1, wherein the one or more detected abnormalities comprise a quantitative deviation or a qualitative deviation from a preconfigured metric for a healthy person.

4. The method of claim 1, wherein the detecting by the computing device of one or more abnormalities in the real-time established relationship between the pregnant mother and the fetus based upon the comparison of the real-time established relationship with the historically established relationships and upon the comparison of the maternal physiological data with pre-pregnancy data of the pregnant mother comprises:

determining if the historically established relationships display one or more associated abnormalities; and determining if the pre-pregnancy data of the pregnant mother implies one or more abnormalities.

5. The method of claim 1, wherein the generated maternal nutrition plan further comprises a list of elements for the pregnant mother to limit intake thereof.

6. The method of claim 1, wherein the maternal nutrition plan is generated by the computing device on an hourly basis, a daily basis, a weekly basis, or a monthly basis.

7. A computer program product for generating a personalized maternal nutrition plan for a pregnant mother, the computer program product comprising:

one or more non-transitory computer-readable storage media and program instructions stored on the one or more non-transitory computer-readable storage media, the program instructions, when executed by a computing device, causing the computing device to perform a method comprising:

receiving real-time maternal physiological data associated with a pregnant mother and real-time fetal physiological data from a fetus within the pregnant mother, wherein the real-time maternal physiological data is detected via a first sensor and comprises a maternal triglyceride level, and wherein the real-time fetal physiological data is detected via a second sensor and comprises a fetal triglyceride level;

receiving real-time environmental data associated with the pregnant mother, wherein the real-time environmental data is detected via a third sensor and is selected from the group consisting of humidity and wind speed;

establishing a real-time relationship between the maternal physiological data, the fetal physiological data, and the environmental data, wherein the real-time relationship comprises a triglyceride relationship of the maternal triglyceride level with respect to the fetal triglyceride level;

comparing the real-time established relationship with historically established relationships between pregnant mothers and fetuses;

comparing the maternal physiological data with pre-pregnancy data of the pregnant mother;

detecting one or more abnormalities in the real-time established relationship between the pregnant mother and the fetus based upon the comparison of the real-time established relationship with historically established relationships and the comparison of the maternal physiological data with pre-pregnancy data of the pregnant mother;

generating a maternal nutrition plan based upon the one or more detected abnormalities, wherein the maternal nutrition plan comprises a list of nutrients in suggested amounts for the pregnant mother to intake and a schedule of when to consume the nutrients;

outputting the generated maternal nutrition plan and the detected one or more abnormalities to a first electronic device associated with the pregnant mother and to a second electronic device associated with a physician; and presenting the maternal nutrition plan and the one or more abnormalities via the first electronic device and via the second electronic device.

8. The computer program product of claim 7, wherein the comparing the real-time established relationship with historically established relationships comprises:

accessing a plurality of historically established relationships between pregnant mothers and fetuses; and selecting one or more historically established relationships with a highest degree of similarity to the established real-time relationship.

9. The computer program product of claim 7, wherein the one or more detected abnormalities comprise a quantitative deviation or a qualitative deviation from a preconfigured metric for a healthy person.

10. The computer program product of claim 7, wherein the detecting of the one or more abnormalities in the real-time established relationship between the pregnant mother and the fetus based upon the comparison of the real-time established relationship with the historically established relationships and upon the comparison of the maternal physiological data with pre-pregnancy data of the pregnant mother comprises:

determining if the historically established relationships display one or more associated abnormalities; and determining if the pre-pregnancy data of the pregnant mother implies one or more abnormalities.

11. The computer program product of claim 7, wherein the generated maternal nutrition plan further comprises a list of elements for the pregnant mother to limit intake thereof.

12. The computer program product of claim 7, wherein the maternal nutrition plan is generated by the computing device on an hourly basis, a daily basis, a weekly basis, or a monthly basis.

13. A computer system for generating a personalized maternal nutrition plan for a pregnant mother, the computer system comprising:

one or more computer processors, one or more computer-readable memories, one or more computer-readable storage media, a first sensor, a second sensor, a third sensor, and program instructions stored on at least one of the one or more computer-readable storage media for execution by at least one of the one or more processors to cause the computer system to perform a method comprising:

receiving real-time maternal physiological data associated with a pregnant mother and real-time fetal physiological data from a fetus within the pregnant mother, wherein the real-time maternal physiological data is detected via the first sensor and comprises a maternal triglyceride level, and wherein the real-time fetal physiological data is detected via the second sensor and comprises a fetal triglyceride level;

receiving real-time environmental data associated with the pregnant mother, wherein the real-time environmental data is detected via the third sensor and is selected from the group consisting of humidity and wind speed;

establishing a real-time relationship between the maternal physiological data, the fetal physiological data, and the environmental data, wherein the real-time relationship comprises a triglyceride relationship of the maternal triglyceride level with respect to the fetal triglyceride level;

comparing the real-time established relationship with historically established relationships between pregnant mothers and fetuses;

comparing the maternal physiological data with pre-pregnancy data of the pregnant mother;

detecting one or more abnormalities in the real-time established relationship between the pregnant mother and the fetus based upon the comparison of the real-time established relationship with historically established relationships and the comparison of the maternal physiological data with pre-pregnancy data of the pregnant mother;

generating a maternal nutrition plan based upon the one or more detected abnormalities, wherein the maternal nutrition plan comprises a list of nutrients in suggested amounts for the pregnant mother to intake and a schedule of when to consume the nutrients;

outputting the generated maternal nutrition plan and the detected one or more abnormalities to a first electronic device associated with the pregnant mother and to a second electronic device associated with a physician; and presenting the maternal nutrition plan and the one or more abnormalities via the first electronic device and via the second electronic device.

14. The computer system of claim 13, wherein the comparing the real-time established relationship with historically established relationships comprises:

accessing a plurality of historically established relationships between pregnant mothers and fetuses; and selecting one or more historically established relationships with a highest degree of similarity to the established real-time relationship.

15. The computer system of claim 13, wherein the one or more detected abnormalities comprise a quantitative deviation or a qualitative deviation from a preconfigured metric for a healthy person.

16. The computer system of claim 13, wherein the detecting of the one or more abnormalities in the real-time established relationship between the pregnant mother and the fetus based upon the comparison of the real-time established relationship with the historically established relationships and upon the comparison of the maternal physiological data with pre-pregnancy data of the pregnant mother comprises:

determining if the historically established relationships display one or more associated abnormalities; and determining if the pre-pregnancy data of the pregnant mother implies one or more abnormalities.

17. The computer system of claim 13, wherein the generated maternal nutrition plan further comprises a list of elements for the pregnant mother to limit intake thereof.

* * * * *